(12) United States Patent
Ward

(10) Patent No.: US 9,867,969 B2
(45) Date of Patent: Jan. 16, 2018

(54) APPARATUS AND METHOD FOR PROVIDING FIXATION OF A LINE TO A SUBJECT

(71) Applicant: FIXIT MEDICAL LTD, Dorset (GB)

(72) Inventor: Robert Douglas Ward, Dorset (GB)

(73) Assignee: FIXIT MEDICAL LTD., Dorset (GB)

( * ) Notice: Subject to any disclaimer, the term of this patent is extended or adjusted under 35 U.S.C. 154(b) by 169 days.

(21) Appl. No.: 14/353,076

(22) PCT Filed: Oct. 19, 2012

(86) PCT No.: PCT/GB2012/052601
§ 371 (c)(1),
(2) Date: Apr. 21, 2014

(87) PCT Pub. No.: WO2013/057508
PCT Pub. Date: Apr. 25, 2013

(65) Prior Publication Data
US 2014/0276658 A1    Sep. 18, 2014

(30) Foreign Application Priority Data

Oct. 21, 2011  (GB) .................................. 1118167.4

(51) Int. Cl.
*A61M 27/00* (2006.01)
*A61M 25/02* (2006.01)

(52) U.S. Cl.
CPC ............ *A61M 27/00* (2013.01); *A61M 25/02* (2013.01); *A61M 2025/028* (2013.01); *A61M 2025/0253* (2013.01); *A61M 2025/0286* (2013.01)

(58) Field of Classification Search
CPC .................. A61M 25/02; A61M 27/00; A61M 2025/0253; A61M 2025/028;
(Continued)

(56) References Cited

U.S. PATENT DOCUMENTS 3,957,082 A    5/1976  Fuson
4,080,970 A *  3/1978  Miller .................... A61M 27/00
                                                                604/174
(Continued)

FOREIGN PATENT DOCUMENTS

GB         2160776       1/1986
GB         1118167.4    10/2011
(Continued)

OTHER PUBLICATIONS

International Search Report dated Jan. 3, 2013 for PCT/GB2012/052601.
(Continued)

*Primary Examiner* — Adam Marcetich
(74) *Attorney, Agent, or Firm* — Fleit Gibbons Gutman Bongini & Bianco PL; Paul D. Bianco; Katharine Davis Wong

(57) ABSTRACT

A device for supporting a surgical line, such as a surgical drain, a catheter or the like, is provided, the device comprising a base having an opening therein for receiving a first line extending from a subject; and a connector mounted to the base and having a first end for connection to an end of the surgical line and a second end for connection to a second line. The device preferably comprises a housing mounted to the base and enclosing the opening in the base, with the connector extending through the housing. The housing or a portion thereof is removable to provide access to the interior of the housing. The housing or a portion thereof is preferably rotatable with respect to the base.

27 Claims, 8 Drawing Sheets

(58) Field of Classification Search
CPC .. A61M 2025/0286; A61M 2025/0246; A61M 1/008; A61M 1/0088; A61F 2013/00412; A61F 2013/00536; A61F 15/008; A61F 2013/00182

See application file for complete search history.

(56) References Cited

U.S. PATENT DOCUMENTS

| | | | |
|---|---|---|---|
| 4,096,853 A * | 6/1978 | Weigand | A61M 25/02 600/431 |
| 4,261,363 A | 4/1981 | Russo | |
| 4,464,178 A * | 8/1984 | Dalton | A61M 39/0208 128/DIG. 26 |
| 4,516,293 A | 5/1985 | Beran | |
| 4,533,349 A * | 8/1985 | Bark | A61M 25/02 128/DIG. 26 |
| 4,632,671 A | 12/1986 | Dalton | |
| 4,659,329 A | 4/1987 | Annis | |
| 4,767,405 A * | 8/1988 | Lokken | A61M 25/02 128/DIG. 26 |
| 4,808,162 A * | 2/1989 | Oliver | A61J 15/0015 128/DIG. 26 |
| 5,112,313 A | 5/1992 | Sallee | |
| 5,215,531 A | 6/1993 | Maxson et al. | |
| 5,562,107 A * | 10/1996 | Lavender | A61F 13/0269 128/888 |
| 5,758,660 A * | 6/1998 | Lokken | A61M 25/0111 128/877 |
| 5,833,666 A | 11/1998 | Davis et al. | |
| 6,231,547 B1 | 5/2001 | O'Hara | |
| 6,287,281 B1 | 9/2001 | Nishtala | |
| 7,635,354 B2 | 12/2009 | Navarro | |
| 2002/0052610 A1* | 5/2002 | Skakoon | A61B 34/20 606/129 |
| 2003/0158539 A1 | 8/2003 | Bouphavichith | |
| 2003/0176835 A1* | 9/2003 | Yamazaki | A61M 1/12 604/93.01 |
| 2003/0199850 A1* | 10/2003 | Chavez | A61M 25/02 604/523 |
| 2005/0222544 A1* | 10/2005 | Weston | A61M 1/0001 604/313 |
| 2006/0025723 A1 | 2/2006 | Ballarini | |
| 2007/0043326 A1* | 2/2007 | Navarro | A61M 25/02 604/264 |
| 2007/0055205 A1* | 3/2007 | Wright | A61F 13/023 604/174 |
| 2007/0112303 A1 | 5/2007 | Liniger | |
| 2007/0173773 A1* | 7/2007 | Stamler | A61B 90/05 604/192 |
| 2007/0249980 A1 | 10/2007 | Carrez | |
| 2008/0015509 A1* | 1/2008 | Backman | A61M 25/02 604/174 |
| 2008/0119802 A1* | 5/2008 | Riesinger | A61F 13/00068 604/313 |
| 2008/0243085 A1 | 10/2008 | DeStefano | |
| 2009/0143763 A1 | 6/2009 | Wyss et al. | |
| 2009/0157157 A1* | 6/2009 | Schorn | A61M 25/02 607/149 |
| 2010/0022975 A1* | 1/2010 | Vanden Bosch | A61F 5/445 604/338 |
| 2010/0286639 A1* | 11/2010 | Scholz | A61F 13/02 604/319 |
| 2010/0298790 A1* | 11/2010 | Guidi | A61M 1/0023 604/319 |
| 2011/0270187 A1* | 11/2011 | Nelson | A61M 25/02 604/151 |
| 2012/0116329 A1* | 5/2012 | Canada | A61M 1/0088 604/319 |
| 2012/0245529 A1* | 9/2012 | Hummen | A61M 25/02 604/175 |
| 2013/0102945 A1* | 4/2013 | Long | A61M 39/0247 602/43 |
| 2013/0231619 A1* | 9/2013 | Wiltshire | A61F 13/02 604/305 |

FOREIGN PATENT DOCUMENTS

| | | |
|---|---|---|
| JP | 2006520628 A | 9/2006 |
| WO | 2001/68180 | 3/2001 |
| WO | 2003075980 | 9/2003 |
| WO | 2006/040461 | 4/2006 |
| WO | 2006/085085 | 8/2006 |
| WO | 2006090148 | 8/2006 |
| WO | 2007/006306 | 1/2007 |
| WO | 2008/017329 | 4/2007 |
| WO | 2008/117078 | 10/2008 |
| WO | 2013057508 | 4/2013 |

OTHER PUBLICATIONS

International Preliminary Report dated Jan. 23, 2014 for PCT/GB2012/052601.
Written Opinion dated Sep. 18, 2013 for PCT/GB2012/052601.
PCT Demand—Response to ISR sent Mar. 22, 2013 for PCT/GB2012/052601.
GB Search Report dated Jan. 30, 2012 for GB 1118167.4.
PCT Communication for PCT/GB2012/052601 dated Nov. 15, 2013.
PCT Communication for PCT/GB2012/052601 dated Oct. 25, 2013.
Response to Written Opinion dated Nov. 18, 2013 for PCT/GB2012/052601.
Further Response to Written Opinion dated Jan. 14, 2014 for PCT/GB2012/052601.
Translation of JP Office Action dated May 15, 2017 for JP patent application No. 2014-536333.

* cited by examiner

APPARATUS AND METHOD FOR PROVIDING FIXATION OF A LINE TO A SUBJECT

The present invention relates to an apparatus for supporting a surgical line extending from an opening in a subject, for example a drain line, and for providing fixation of the line to the subject.

Many medical procedures conducted on a subject require the subject to be provided with a line, such as a surgical drain or a drainage catheter, extending into the subject through an opening formed in the skin of the subject. Such lines are usually for the delivery of fluids to the subject or the removal of fluids from the subject. One example of such a line is a drain placed into the body of the subject to remove fluids therefrom, for example at the site of a wound or after surgery. Such drain lines are inserted into the body of the subject through an incision made in the skin, with the open end of the drain within the body being positioned to receive fluid from the target site. The fluid may be allowed to drain from the subject under the action of gravity using a passive drain system. Alternatively, the fluid may be drawn from the subject using an active drain system, for example by connecting the distal end of the drain line to a suitable vacuum pump.

In practice, drain lines are secured to the subject after insertion and placement. In many cases, the drain line is inserted through an incision and is secured to the skin of the subject using sutures, for example as part of or in addition to the procedure for closing the incision. Alternatively, or in addition thereto, the drain line is secured to the skin using adhesive tape or, a commercially available fixation device. A particular problem with drain lines is that they may become dislodged, for example as a result of movement of the subject. This can result in the line losing its correct placement within the subject and, in extreme cases, the line being pulled out of the subject.

Devices for supporting lines, such as drain lines, are known in the art.

US 2006/0025723 discloses an antibacterial chest tube, surgical drain, port or access line securing device. The device comprises a main body portion or base of a generally oval shape. A plurality of holes are formed in the periphery of the base to allow the device to be secured to the skin of a patient by means of sutures. The device comprises a tubular element extending from the surface of the base, the tubular element and the base defining a generally tubular bore extending therethrough for accepting a drain tube or the like. The tubular element may extend perpendicular from the base or at an angle to the perpendicular. The device comprises a means for securing a drain tube or the like within the tubular element. US 2006/0025723 discloses several different embodiments of the securing means. In a first design, a pair of locking screws are provided, which extend through threaded bores in the tubular element and can be tightened to grip the outer surface of the drain tube within the tubular element. In an alternative arrangement, the tubular element is provided with an inflatable inner collar, which may be inflated using liquid or gas, to grip the drain tube and hold it in position within the bore of the tubular element.

U.S. Pat. No. 4,516,293 discloses a clamping structure for holding a tube having a base and a wrap-around strap.

An adjustable drainage tube holder is disclosed in GB 2,160,776 and comprises a clear flexible mounting plate for attachment to the patient by a suitable adhesive. A collar extends from the mounting plate and is aligned with an aperture in the plate, the collar accepting a tube when in use.

U.S. Pat. No. 6,231,547 discloses an external retaining device for a catheter. The device has a base member provided with a passage therethrough. A tube guide extends from the base and has an elongate channel therein. A manually operable clip is provided to secure the catheter in the channel in the tube guide.

WO 01/68180 discloses a device for securing a catheter or the like to a subject, the device comprising a base, a cover and a compressible member having a receptacle into which the catheter or the like is placed and held when the cover is closed.

U.S. Pat. No. 4,261,363 concerns a retention clip for body fluid drains having an upper portion provided with a longitudinal slot into which the drain tube maybe inserted from one side after placement of the drain tube in the drainage site on the subject. The clip has a base portion, by which the clip may be secured to the subject, for example by way of tape.

A device for fixing on the skin of a catheter exiting a cutaneous emergence site is disclosed in WO 2006/040461. The device comprises a flexible pad having a housing and a hole therethrough. A slot extends across the pad, allowing the pad to be slid around a catheter extending from a subject to have the catheter extend through the hole. A foldable side tab with a cap is provided to close the housing.

WO 2006/085085 discloses a device for securing a tube to the skin of a subject and having a flexible base or plaster component for adhering to the skin, a support protruding from the base for supporting a tube, and a flexible cover for securing over the support and tube. A similar device is shown and described in WO 95/33508.

WO 2008/017329 discloses a fixation device for holding a medical instrument, such as a trocar, having a flexible sheet-like member having an aperture and a slot for receiving the instrument.

An access port is disclosed in WO 2007/006306 and comprises a sleeve surrounding an aperture for receiving a tube, a flange portion and a membrane. The access port is described as being suitable for use with a wound care device or a drainage bag.

WO 2008/117078 discloses a dressing for supporting a tube extending from an incision in a subject, the dressing having a based and a support for holding the tube in position.

A cannula skirt is described and shown in U.S. Pat. No. 5,215,531 and comprises a generally conical skirt having an opening therein for receiving a cannula. A collar extends from the skirt and comprises a clamp for fastening the collar around the cannula, once in position.

U.S. Pat. No. 5,833,666 discloses a catheter fixation assembly for securing a catheter at or adjacent to en exit site on a subject's body. The assembly comprises a resilient member for fixing to the subject and an adjustable clamp. In one embodiment, the assembly comprises a clamp assembly that allows the catheter to be secured so as to extend along the body of the subject. However, this embodiment of the assembly is required to be fixed to the subject some distance from the exit site or opening in the subject. This is undesirable.

Known devices for securing drain lines, such as those discussed above, go some way towards addressing the aforementioned problems of conventional practices. However, a number of issues remain. In general, the known devices rely upon some form of clamp or other means to grasp the line. As the line is generally a flexible tube, this can cause the bore of the tube to be partially occluded, reducing the effectiveness of the line in transporting fluids, and, in extreme cases, fully closing and blocking the line. Alternatively, for example when trying to avoid occluding the line, the device can provide insufficient grip on the line to hold it securely, in turn resulting in the line being dislodged.

There is a need for an improved device for supporting a line, such as a drain line, when in place in a subject.

The invention is defined in the appended claims.

According to the present invention, in a first aspect there is provided a device for supporting a separately placed surgical line, the device comprising:

a base having an opening therein for receiving a separately placed first surgical line extending from a subject;

a connector mounted to the base and having a first end for connection to an end of the said first surgical line and a second end for connection to a second line; and;

a housing extending from the base, the housing arranged to form an enclosure for the base and for the opening in the base.

The device of this aspect of the present invention comprises a base. The base may be any suitable shape. A particularly suitable shape is generally rounded, in particular circular. However, other shapes may also be used.

The base is provided with an opening therein. In use, the opening receives a first line, such as a drain tube, extending from the subject. Further, in use, the device is preferably located on the subject so as to have the opening in the base of the device extend over the opening, such as an incision, in the subject out of which the line is extending. The opening in the base may be any suitable shape and size to receive the first line, as aforementioned. In one preferred embodiment, the opening is generally circular. However, the opening may be other shapes, as appropriate.

The base may be provided with a slit or slot therein, extending from an edge of the base to the opening therein, to allow the base to be slid onto the line from the side, for example close to the subject.

The device comprises a housing. The housing connected to and extends from the base and the housing extends over the opening in the base, enclosing the opening in the base. In this way, with the device secured to the skin of the subject over the incision or other opening in the subject, the housing provides protection for the entry site of the line into the subject, for example protection against infection.

In addition, the housing, by extending over and covering the entry site of the line in the subject, prevents the line and its entry site being tampered with, for example by the subject.

In an embodiment the housing is a hollow enclosure and the housing and enclosure are arranged to provide clearance spacing between a first surgical line extending from a patient and a first end of the connector, wherein the clearance spacing is configured such that the said first surgical line may be connected to the connector and coiled within the housing.

The housing and enclosure of an embodiment are arranged to provide clearance spacing extending around a first surgical line extending from a patient and a first end of the connector, wherein the clearance spacing is configured such that the said first surgical line may be connected to the connector and coiled within the housing. The housing provides a space suitable for accommodating a length of surgical line exiting the subject and for connecting to a first end of the connector.

Further, the housing may be of a size to accommodate therein any excess or surplus length of the line that is not required in use. For example, the surplus length of line may be coiled or folded inside the housing. In this way, the excess line is kept housed and is not exposed, preventing the line from being caught or snagged in use by the subject or another person. In an embodiment the housing and enclosure are arranged to provide sufficient space and clearance within the housing to permit any excess or surplus length of a separately placed first surgical line to be coiled within the housing prior to attachment to the connector.

The facility to coil and house the line is advantageous as many surgical lines have standard lengths prior to insertion. Therefore if the intended target point for the surgical line is relatively superficial within the subject then there will accordingly be a greater length of the line extending out of the subject than if the target had been deeper. To avoid excess line protruding in an untidy or potentially hazardous way the excess length is neatly coiled within the space created within the housing prior to attachment to the connector.

The space and clearance is such that the line can be accommodated in this coiled arrangement within the housing and then held securely at the connector so that there are no transfer of forces from the second surgical line to the first and vice versa. This means that there is no pulling force exerted on or transferred to the line exiting the subject. In this way should the length of surgical line be snagged (either of the first or the second surgical lines, by the subject or by a member of the medical team) the damage to the entry site of the line into the subject, or to the lines or other medical equipment is reduced and minimised.

The device may be secured to the skin of a subject by means of the base. Accordingly, the base is preferably provided with attachment means for securing to the skin of the subject. Such means include, for example, an adhesive layer on a portion or all of the first surface of the base. Alternatively, or in addition, the base may be provided with one or more openings therein or loops extending therefrom, to allow the base to be secured to the skin of the subject by sutures. The additional openings in the base and extending therefrom in an embodiment are adjacent the central opening in the base to allow the base to be secured to the skin of the subject by sutures As a further alternative or in addition to the aforementioned means, the device may comprise one or more straps for securing the device to the subject. The straps may be secured to the device in any suitable manner. For example, the base may be provided with one or more openings therein or loops extending therefrom to which one or more straps may be attached.

In use, the device may be additionally secured to the subject by means of one or more portions of adhesive tape applied to the second surface of the base and the adjacent skin of the subject.

The base may comprise a generally flat first surface which, in use, is disposed towards or against the skin of the subject, and a second surface disposed away from the skin in use. To allow the device to conform better to the skin of the subject and, for example, to allow for movement of the subject, the base is preferably flexible. A portion of the base of an embodiment is flexible, so that the remaining base may be rigid. In order for the device to be placed and arranged on a curved portion of the subject in this embodiment a flexible adherent layer is physically attached to a portion only of the rigid base. Suitable materials for forming the base are known in the art and are commercially available. Suitable materials include a range of medical grade polymers.

The device of an embodiment further comprises a connector mounted to the second surface of the base. The connector may be mounted directly to the base. Alternatively, the connector may be mounted indirectly to the base, for example being mounted to a housing attached to the base, as described hereinbelow. Mounting the connector to a housing as described below is particularly preferred.

The connector has a first end, to which the distal end of the line extending from the subject is connected in use. The connector has a second end, to which is connected an end of a second line. The connector further comprises a conduit extending between the first and second ends, through which fluids may flow between the first and second lines.

The connector may comprise any suitable form for its first and second ends for connection to the respective lines. Part of the connector may comprise flexible tubing. It is known that some surgical lines if tightly coiled can kink if the bends are too acute. This may occur when attaching the end of the first surgical line to the connector. By providing part of the connector between the first and second ends with flexible tubing this overcomes the problem as it allows the first surgical line to form a less tight coil with a less acute bend, thus minimising the chances of kinking.

In particular, the form of connection at the first and second ends is such that the line being connected is not required to be clamped or crushed. This is achieved, for example, by providing the end of the connector and the end of the respective line with suitable male and female connector portions. Such connector portions are known in the art. Preferably, the first end comprises a standard Luer connector, more preferably a male Luer connector, for connection to a corresponding Luer connector provided on many lines, such as drain tubes. Preferably, the second end comprises a standard Luer connector, more preferably a female Luer connector, for connection to a corresponding Luer connector provided on the second line. Such Luer connectors and their form, in particular a body having a Luer taper provided therein, are widely used and are well known to the skilled person.

This means that the first line is physically attached to the housing via the connectors and the result seen is that no clamping or crushing of the line is required is required in order to attach the line. The reduction in the occurrence of clamping or crushing prolongs the lifetime of the equipment and improves the safety of the procedure for the subject. The separately placed line with connector secured at the housing and not with a clamp improve equipment lifetime and allow the connector portion inside the housing and any excess length of line to be coiled within the housing.

The connector may be formed from any suitable material. Suitable medical grade polymers are well known in the art. In particular, the connector may be formed from a polymer having a greater hardness than the lines or tubes connected thereto.

With the connector being connected to the base or to the housing, in particular in a manner that avoids the connector being clamped or crushed, the need to clamp any part of the series of lines and the connector is avoided. In this way, the risk of occluding or blocking a line through use of the device is avoided.

In one preferred embodiment, the connector is provided with means to release the connection of the first line to the second line at a predetermined force. The predetermined force is less than that required to break another connection in the lines and is less than the force required to disturb or dislodge the device from the skin of the subject. In this way, an inadvertent pull on a line, for example as a result of a sharp movement of the subject, does not disturb the placement of the line in the subject, avoiding possible injury to the subject.

In one preferred embodiment of the invention, the housing is removably connected to the base and/or comprises a portion that is removable to provide access to the interior of the housing. Access to the interior of the housing is required when the separately placed first line is connected. For example, the housing may be provided with a housing body and a removable portion such as a lid or cover. In this way, access may be obtained to the entry site of the line into the subject, for example to allow the entry site to be examined, such as to monitor for infection of the subject. In addition, this allows access to the interior of the housing.

The removable portion, such as a lid or cover, of the housing may be connected to the housing body in any suitable manner. Suitable means for removably fastening the removable portion to the housing body are known in the art and include, for example a threaded connection or a hinge.

The housing may be entirely opaque. More preferably, the housing comprises at least a portion that is transparent, allowing the interior of the housing to be viewed. This is particularly advantageous in embodiments in which the housing extends over the opening in the base and the opening, such as an incision, in the subject. In this way, the condition of the incision or the like in the subject and the entry site of the line into the subject may be readily inspected. In addition the coiled tubes in the housing can also be inspected. In embodiments in which the housing is provided with a removable portion, such as a lid or cover, the removable portion may be partially or wholly transparent.

Further, the housing is preferably provided with one or more openings or apertures therein to provide ventilation to the interior of the housing. Again, this is particularly preferred when the housing extends over the opening in the base and the opening, such as an incision, in the subject. In embodiments in which the housing is provided with a removable portion, such as a lid or a cover, such one or more openings or apertures may be provided in the removable portion.

As noted above, the device of the present invention comprises a connector. In a particularly preferred embodiment, the housing extends over the opening in the base of the device and the connector is provided in the body of the housing, in particular with its first end inside the housing and its second end outside the housing and the conduit of the connector extending through the housing body. In this way, the portion of the first line extending from within the subject is retained wholly within the housing and is connected at its end to the first end of the connector. The second line is connected to the second end of the connector outside the housing.

The housing may be provided with a single connector. Alternatively, a plurality of connectors, for example two, three or four connectors, may be provided, for example spaced around the housing. In this way, the device may provide alternative positions for the lines, so as to best suit the situation of the device and the opening in the subject. Alternatively, the plurality of connectors may allow the device to be used with more than one line, in particular where a plurality of lines extend from openings in close proximity or when a single line possesses more than one channel.

The fact that the 1st line is physically attached to the housing via the connectors means no clamping or crushing of the line is required or occurs. The separately placed line and housing mean that the connector with any excess length of connector or line can be coiled within the housing.

In a further preferred embodiment, the body of the housing is arranged to rotate relative to the base of the device. More specifically, the portion of the housing body provided with the connector is arranged to rotate relative to the base.

In this way, regular movements of the subject may be accommodated, without applying any unusual or excessive tension or force to the first line extending into the subject or to the device. The housing or portion thereof may be arranged to rotate through any suitable angle relative to the base. Preferably, the housing or portion thereof is arranged to rotate through at least 50°, more preferably at least 75°, still more preferably at least 90°, relative to the base. In one preferred embodiment, the housing is limited in its rotation to an arc of from 45 to 180°, more preferably from 60 to 150°, still more preferably from 70 to 120°, more particularly about 90°. In an alternative embodiment, the housing is mounted to the base so as to be able to rotate fully with respect to the base.

It is particularly preferred that the housing or portion thereof is rotatable through an angle of at least 90° relative to the base. A subject in a lying or supine, position generally has a line extending downwards away from the subject, that is substantially perpendicular to the longitudinal axis of the subject, under the action of gravity. However, when the subject rises, such as sitting or standing up, the line generally falls, again under the action of gravity, to extend longitudinally. By mounting the housing or a portion thereof to be rotatable about the base, such movement of the subject is accommodated without applying a force to the lines or the device. In use, to further accommodate such movement of the subject, the portion of the first line extending from the entry site and retained within the housing is of sufficient length to allow the housing portion and the connector to rotate. Preferably, the first line is coiled within the housing, when the device is in use, as described above.

Suitable arrangements for having the housing or a portion thereof rotatable with respect to the base include providing one of the fixed and rotatable components with a channel or groove therein and the other component with a detent for engaging with the channel or groove. In one preferred arrangement, the channel is provided in the base and the detent provided on the housing.

Other arrangements for rotatably mounting the housing or a part thereof will be apparent to the person skilled in the art.

In one embodiment, the arrangement for allowing the housing or portion thereof to rotate with respect to the base also allows the housing or the said portion to be removed from the base.

The housing may be formed from any suitable material. Suitable medical grade polymers are well known in the art and are commercially available.

The housing may have any suitable size and shape. As noted, the housing should be of sufficient size to hold the portion of the first line extending from the subject therein. In one preferred embodiment, the housing is of a size to extend over only a portion of the base, leaving one or more portions of the base extending laterally from the housing, for example to provide a means for securing the base to the skin of the subject, as described above.

The housing may have any suitable shape. One preferred form for the housing is a dome.

As noted above, it is particularly advantageous to have the device able to accommodate movement of the subject, in particular movement between a lying (supine) position and an upright position. Accordingly, in an embodiment there is provided a device for supporting a surgical line, such as a drain line, the device comprising:

a base having an opening therein for receiving a first line extending from a subject;

a connector mounted to the base and having a first end for connection to an end of the surgical line and a second end for connection to a second line;

wherein the connector is movable in an arc with respect to the base.

Other features and details of the device of this aspect of the invention are as described above. In particular, the connector may be indirectly mounted to the base by way of a housing, as described above.

As also noted above, it is particularly advantageous to have the device provided with a housing through which the lines extend and to have the housing or a portion thereof rotatable with respect to the opening in the base. Accordingly, in an embodiment, the present invention provides a device for supporting a surgical line, such as a drain line, the device comprising:

a base having an opening therein for receiving a line extending from a subject;

a housing extending over the opening in the base, a portion of the housing being rotatable with respect to the base, the portion of the housing comprising an opening therein through which a line may extend, the opening in the portion of the housing being disposed in the housing such that the opening in the housing is moveable in arc about the opening in the base as the housing rotates.

The housing comprises an opening through which the line may extend. For example, the line may extend from an opening in the body of the subject into the housing interior, and then extend from the housing interior to the exterior of the housing through an opening or port in the housing. More preferably, the opening in the housing is provided with a connector, as described hereinbefore, such that the free end of the line extending from the subject is connected to the first end of the connector within the housing. A further connection piece may be used to connect the free end of the line extending from the subject to the first end of the connector within the housing. The connector in an embodiment is fixed and connected to the housing. A second line is then connected to the second end of the connector outside the housing, as described above.

In this way, a line, such as a drainage catheter may have its entire portion external of the subject held within the housing. The line is connected to a second line via a connector extending from the exterior of the housing, through which fluid may be provided to or removed and carried away from the subject in the normal manner. The line of an embodiment is connected and physically attached to the housing body.

Other features of the device of this aspect of the invention are as described above.

Embodiments of the present invention will now be described, by way of example only, having reference to the accompanying drawings, in which.

Figure 2:
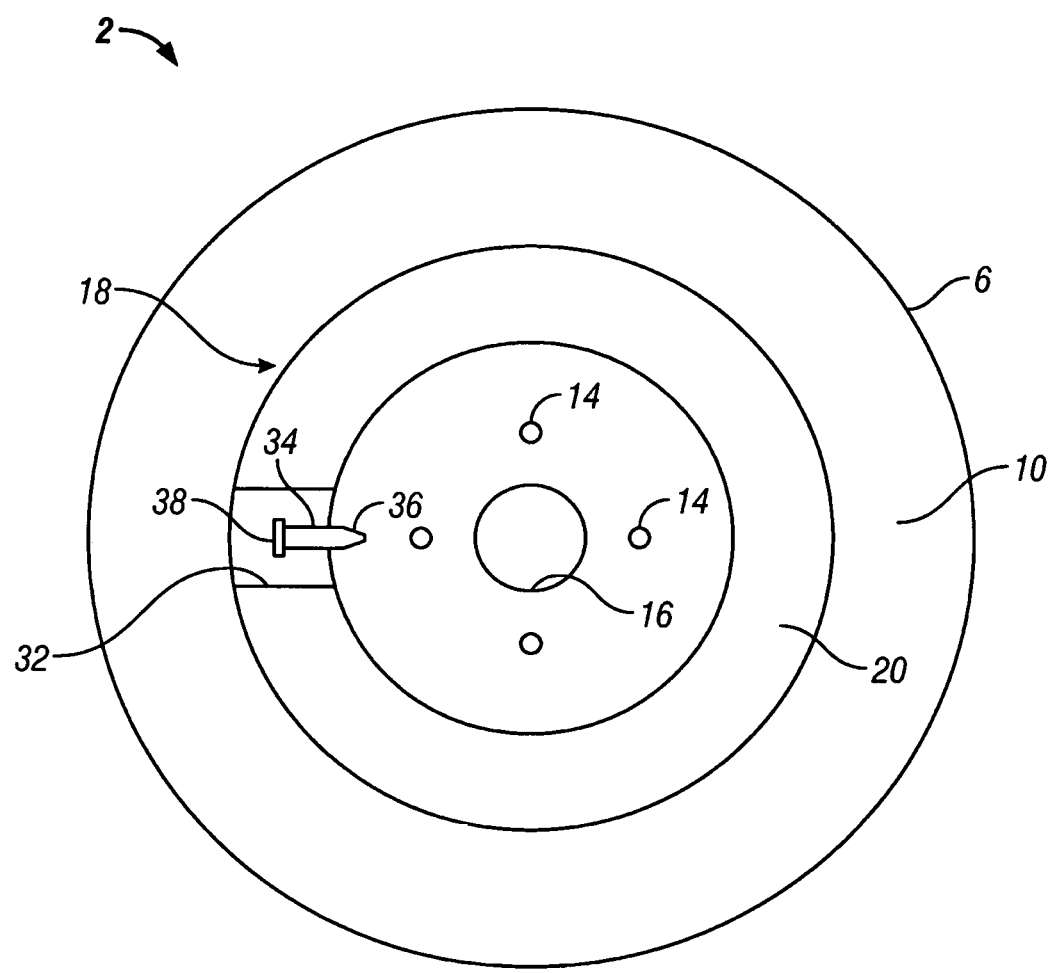
FIG. 2 is a plan view of the device of FIG. 1 with the housing cover removed to show the interior of the housing.

Turning to the accompanying Figures, there is shown a device, generally indicated as 2 secured to the skin 4 of a subject. The device 2 comprises a generally circular base 6 of flexible polymer having a first surface 8 disposed against the skin 4 and a second, exposed surface 10. The base 6 is provided with a layer 12 of medical grade adhesive on its first surface 8 to secure the device to the skin of the subject. Additionally, the device may be secured by means of adhesive tape applied to the edge portion of the second surface 10 and the adjacent skin 4 and/or by means of sutures extending through suitable openings 14 in the base (shown in FIGS. 2 and 3).

Figure 3:
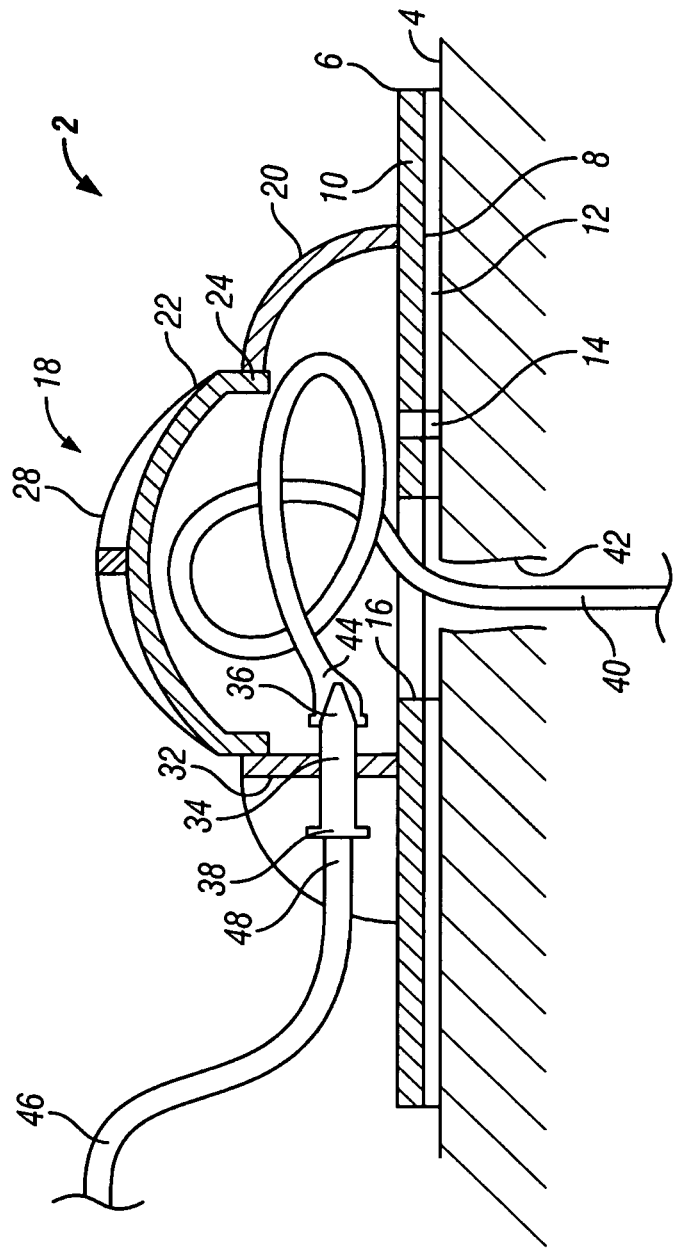
FIG. 3 is a side cross-sectional view of the device of FIG. 1 in position on the skin of a subject and supporting a surgical drain line.

The base 6 is provided with a generally circular opening 16 at its centre, as shown in FIG. 3.

A generally domed circular housing 18 is mounted to the base 6 and extends from the second surface 10 thereof. The housing 18 comprises a housing body 20 and a housing cover 22, releasably secured to the housing body by a threaded flange 24, as shown in FIG. 3. The housing cover 22 is provided with transparent quadrant portions 26, separated from each other by ribs 28. In use, the interior of the housing 18 may be viewed through the transparent quadrant portions 26. The ribs 28 allow the housing cover 22 to be gripped by a user, to facilitate rotation and removal or replacement of the cover. The housing cover 22 is further provided with ventilation holes 30.

The housing body 20 is provided with a recess 32 in its outer surface. A connector assembly 34 extends through the housing body 20 and has a first end 36 provided with a male Luer connector of standard configuration within the housing 18, a conduit extending through the housing body 20, and a second end 38 disposed within the recess 32 outside the housing provided with a female Luer connector of standard configuration.

In use, the device 2 is secured to the skin 4 of the subject about the entry site of a first line, for example a drain 40 placed in the subject through an opening, such as an incision 42 in the skin 4, as shown in FIG. 3. The drain 40 extends from the incision 42 and is coiled within the housing 18. The free or distal end 44 of the drain is provided with a female Luer connector of standard configuration and is connected to the first end 36 of the connector 34. A second line, such as a drain 46 is connected by means of a male Luer connector at an end 48 to the second end 38 of the connector 34 in the external recess 32 of the housing body. Once the drain 40 is in place within the housing, the housing cover 22 is replaced. While the device is in place on the subject, the proper placement of the drain 40 at the entry site and within the housing may be viewed through the transparent portions 26 of the cover. If required the entire housing and device is transparent.

Figure 4:
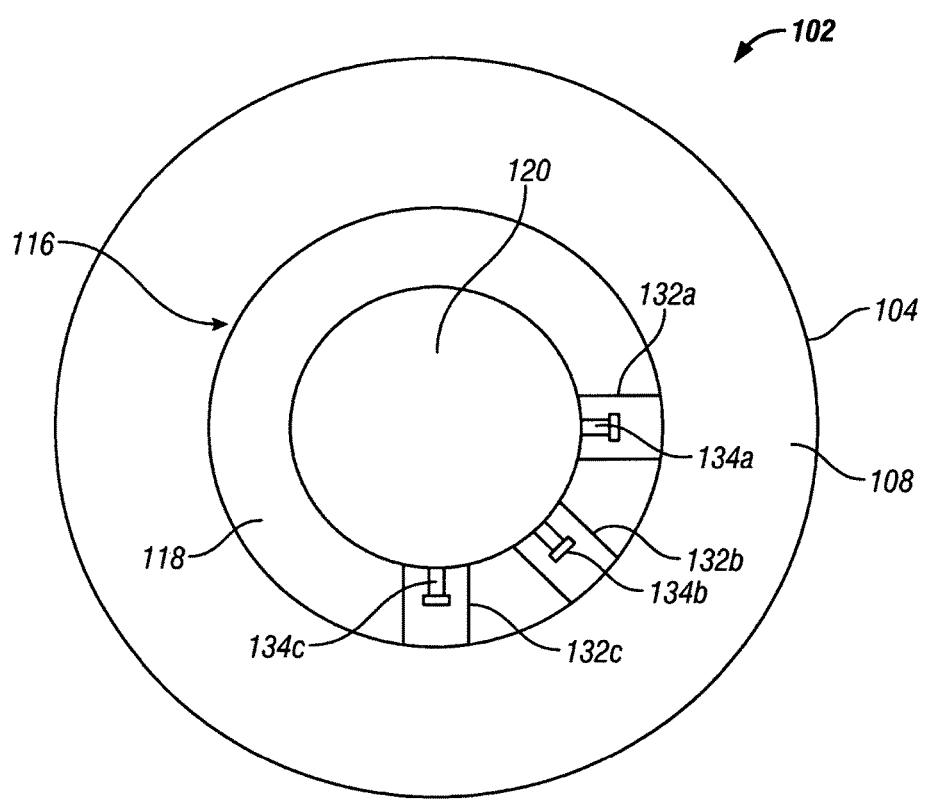
FIG. 4 is a plan view of a device according to a second embodiment of the present invention.
Figure 5:
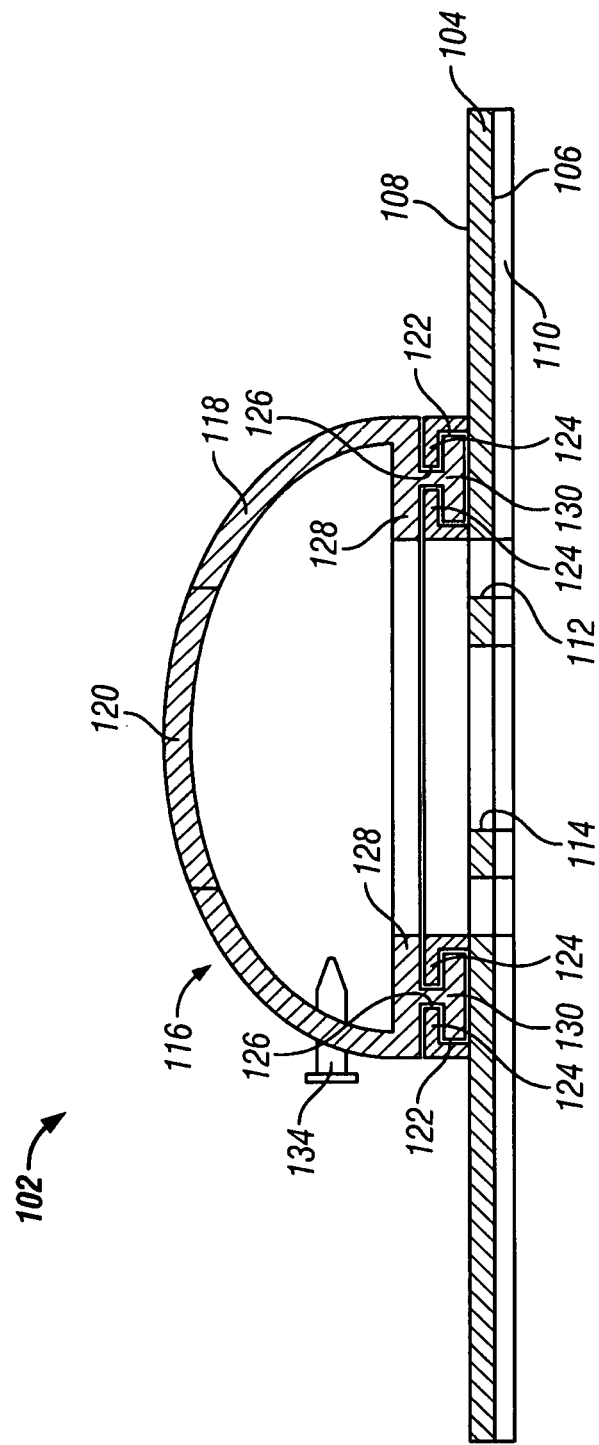
FIG. 5 is a side cross-sectional view of the device of FIG. 4.
Figure 6:
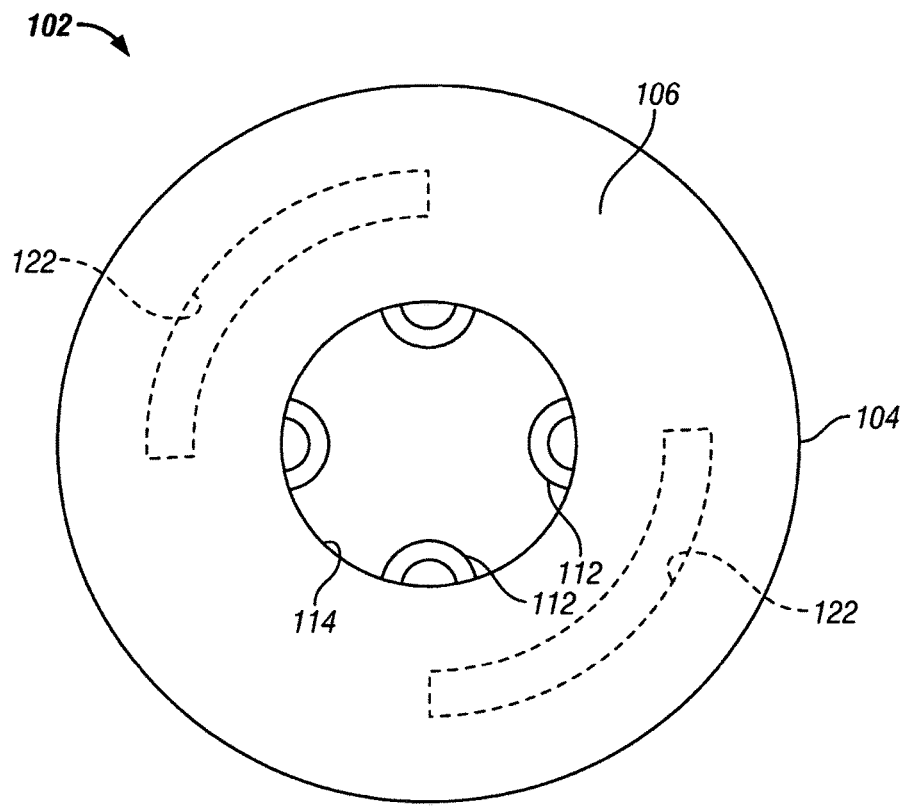
FIG. 6 is a view of the first surface of the base of the device of FIG. 4.

Turning to FIGS. 4 to 6, there is shown a second embodiment of a device according to the present invention, generally indicated as 102. The device 102 comprises a generally circular base 104 of flexible polymer having a first surface 106 disposed against the skin 4 and a second, exposed surface 108. The base 104 is provided with a layer 110 of medical grade adhesive on its first surface 106 to secure the device to the skin of the subject. Additionally, the device may be secured by means of adhesive tape applied to the edge portion of the second surface 108 and the adjacent skin 4 and/or by means of sutures extending through loops 112 extending from the base (shown in FIGS. 5 and 6).

The base 104 is provided with a generally circular opening 114 at its centre, as shown in FIGS. 5 and 6.

Figure 1:
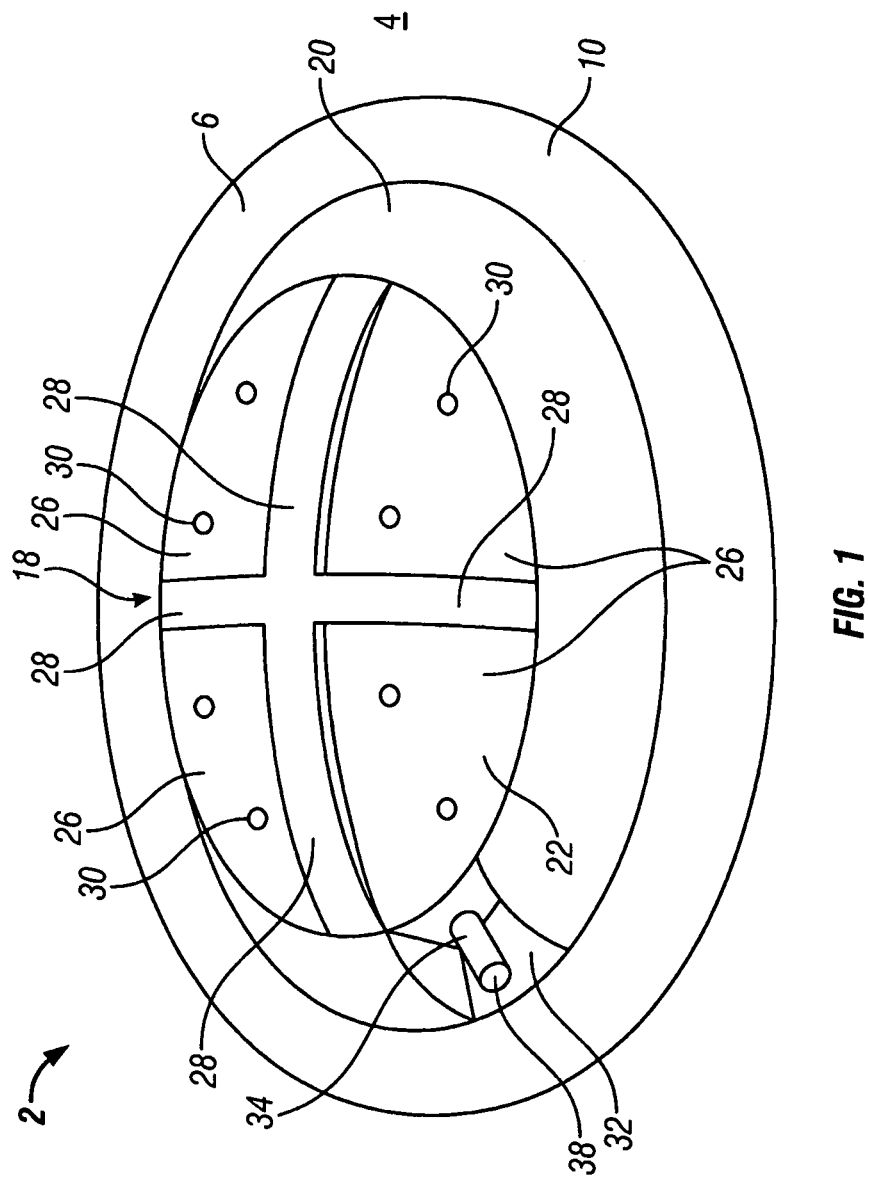
FIG. 1 is a perspective view of a device according to a first embodiment of the present invention on the skin of a subject.

A generally domed circular housing 116 is mounted to the base 104 and extends from the second surface 108 thereof. The housing 116 comprises a housing body 118 and a housing cover 120, releasably secured to the housing body by a threaded connection, as shown in FIG. 5. The housing cover is generally as described hereinbefore and shown in FIGS. 1 to 3.

The housing body 118 is rotatably mounted to the base as follows. The base 104 is provided with arcuate channels 122, shown in cross-section in FIG. 5 and as indicated by dotted lines in FIG. 6. Each channel is provided with a pair of opposing guides 124 defining a slot 126 therebetween. The housing body 118 is provided with a base flange 128 having arcuate guide members 130 extending therefrom. In use, the guide members 130 are slidably retained in a corresponding guide 124 and retained therein by the respective guides 124. The housing body 118 is thus rotatable with respect to the base 104 by having the guide members 130 slide in their respective channels 122. As shown in FIGS. 5 and 6, each arcuate channel 122 on the base 104 and the corresponding guide on the housing body 118 extend through an arc of 90°, to provide about 90° of rotation of the housing 116 relative to the base. The arc of available rotation of the housing may be increased or decreased, for example, by appropriate changes in the length of the channels 122 on the base and/or changes in the size or relative positions of the guide members 130.

The housing body 118 is provided with three spaced apart recesses 132a, 132b, 132c in its outer surface. A connector assembly 134a, 134b, 134c extends through the housing body at each recess 132a, 132b, 132c in the manner as generally described above. In this way, a single device may be used in conjunction with more than one line extending from the subject, as noted above. One of the connectors or more than one connector can possess a plurality of channels. Alternatively when a single surgical line possesses more than one channel the channels can be separately connected to more than one connector. This can provide for a tidy and self-contained arrangement of lines and apparatus leaving a subject and in and around an exit point.

In use, the device 102 is secured to the skin 4 of a subject about an opening, such as an incision in the manner described above. A surgical drain extending from the incision is connected within the housing to the first end of one of the connectors 132a, 132b, 132c and the device employed as described above. The device is oriented on the subject and the selection of the connector to be used is determined by the position of the device on the subject, the expected movement of the subject and the rotation of the housing required to accommodate such movement.

Figure 7:
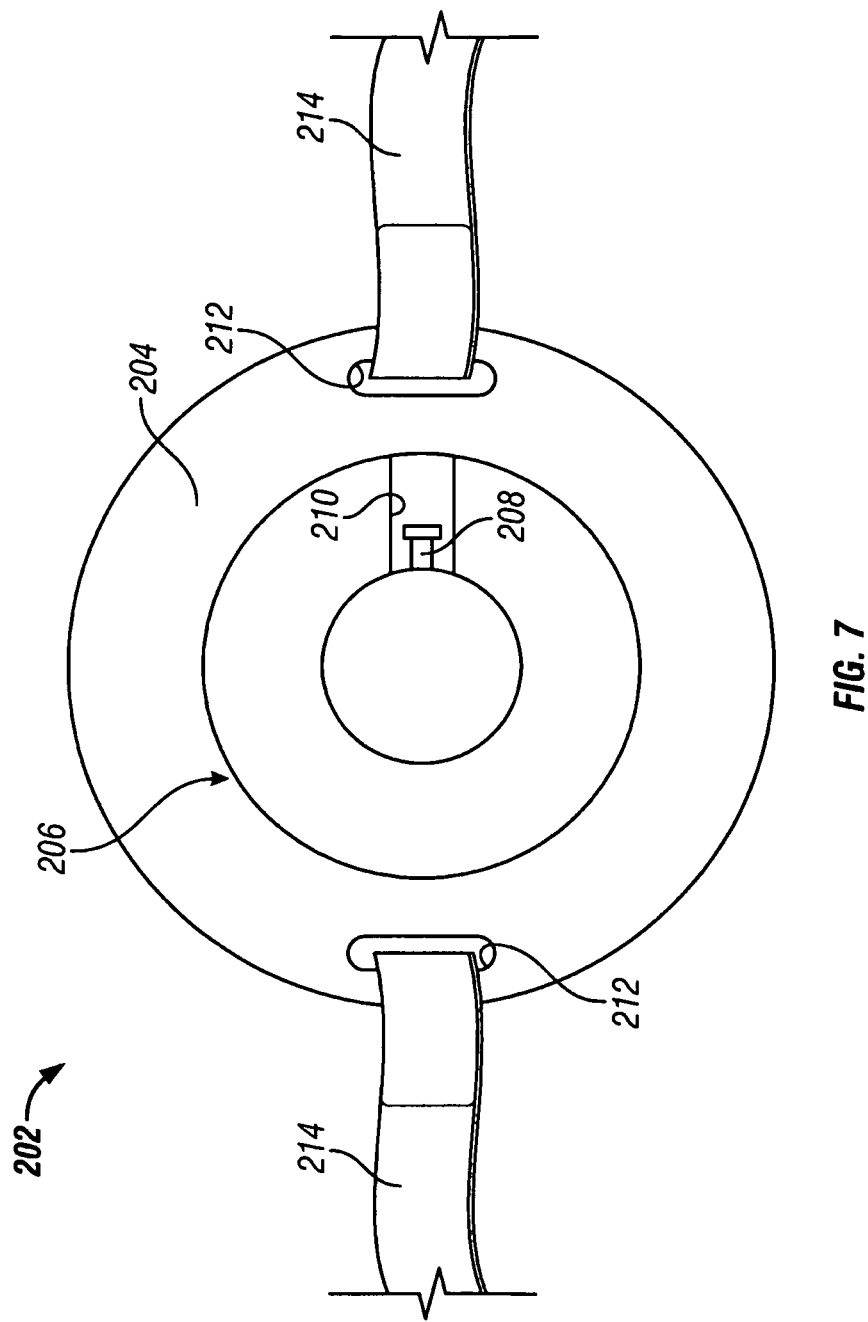
FIG. 7 is a plan view of an embodiment of the device of the present invention provided with securing straps.
Figure 8:
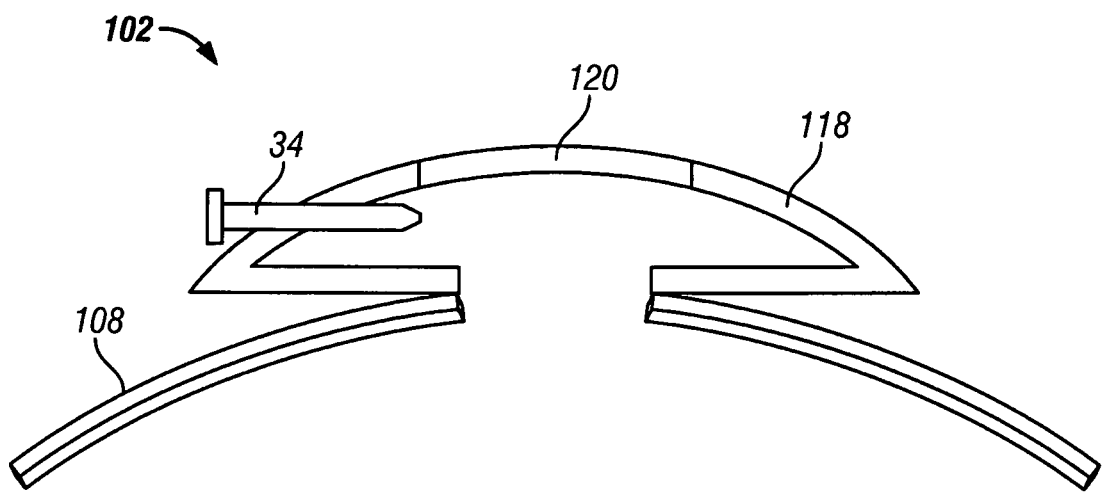
FIG. 8 is a side cross-sectional view of the device of FIG. 4 in an alternative configuration.

Turning to FIG. 7, there is shown a plan view of a device according to the present invention. The device, generally indicated as 202, comprises a generally circular base 204 and a housing assembly 206 mounted thereto. The base and housing may have the configuration of one of the aforementioned embodiments, with the housing being provided with at least one connector assembly 208 in a recess 210. To secure the device to a subject, the base 204 is provided with opposing slots 212 in its edge portion, to which are secured straps 214, in a known manner.

The device 202 is used and operates as described above.

The invention claimed is:

1. A device for supporting a separately-placed surgical line, the device comprising:

a base having an opening therein for receiving a separately-placed first surgical line extending from a subject;

a housing extending from the base, the housing arranged to form an enclosure for the base and for the opening in the base; and a connector immovably fixed within a wall of the housing and having a first end for connection to an end of the first surgical line and a second end for connection to a second line, wherein the housing has a removable lid to provide access to the enclosure, the lid removable from the housing while the housing remains connected to the base.

2. The device according to claim 1, wherein the housing and the enclosure are arranged to provide clearance spacing between the first surgical line extending from the subject and the first end of the connector, the clearance spacing configured such that the first surgical line is connected to the connector at the first end and coiled within the housing.

3. The device according to claim 1, wherein the housing and the enclosure are arranged to provide clearance spacing extending around the first surgical line extending from the subject and the first end of the connector, the clearance spacing configured such that the first surgical line is connected to the connector at the first end and coiled within the housing.

4. The device according to claim 1, further comprising an attaching element or elements for attaching the base to skin of the subject.

5. The device according to claim 4, wherein the attaching element comprises a layer of adhesive on at least a portion of the base.

6. The device according to claim 4, wherein the attaching elements comprise one or more openings in the base or one or more loops extending from the base.

7. The device according to claim 1, wherein the first surgical line extending from the subject to the connector and the second line are connected to the connector without clamping or crushing the lines.

8. The device according to claim 1, wherein at least one of the first and the seconds ends of the connector comprise a Luer connector.

9. The device according to claim 8, wherein both of the first and second ends of the connector comprise Luer connectors, one of the Luer connectors a male Luer connector and the other of the Luer connectors a female Luer connector.

10. The device according to claim 1, wherein the housing is removable from the base or at least a portion of the housing is removable from the base to provide access to an interior of the housing.

11. The device according to claim 1, wherein at least a portion of the housing is transparent.

12. The device according to claim 11, wherein the transparent portion is removable from the base.

13. The device according to claim 1, wherein the housing comprises one or more openings therein to provide ventilation to an interior of the housing.

14. The device according to claim 13, wherein the one or more openings are disposed in a removable portion of the housing.

15. The device according to claim 1, wherein the connector extends through the housing such that the first end of the connector is within the housing and the second end of the connector is outside the housing.

16. The device according to claim 15, wherein the connector comprises a plurality of connectors extending through the housing.

17. The device according to claim 1, wherein at least a portion of the housing is rotatable with respect to the base.

18. The device according to claim 17, wherein the connector extends through the housing and through the rotatable portion.

19. The device according to claim 18, wherein the housing comprises an opening therein through which a line can extend, the opening disposed in the housing such that the opening is moveable in an arc about the opening in the base as the housing rotates.

20. The device according to claim 17, wherein the rotatable portion of the housing is rotatable through an angle of at least 90°.

21. The device according to claim 17, wherein one of the housing or the base comprises a channel and the other of the housing or the base comprises a detent, the detent engaging with the channel to rotatably connect the housing to the channel.

22. The device according to claim 1, wherein the connector is moveable in an arc with respect to the base.

23. The device according to claim 1, wherein part of the connector comprises flexible tubing.

24. A method for supporting a surgical line, the method comprising:

securing the device of claim 1 to skin of a subject about an entry site of a first surgical line;

connecting a first end of the first surgical line to the connector; and coiling at least a portion of the first surgical line within the housing.

25. A method for supporting a surgical line, the method comprising:

providing a device including;
  a base having an opening therein for receiving a separately-placed first surgical line extending from a subject;
  a housing extending from the base, the housing arranged to form an enclosure for the base and for the opening in the base;
  a connector immovably fixed within a wall of the housing and having a first end for connection to an end of the first surgical line and a second end for connection to a second line; and
  a lid providing access to the enclosure, the lid removable from the housing while the housing remains connected to the base;

securing the device to skin of the subject about an entry site of the first surgical line such that the first surgical line extends through the opening in the base;

connecting the first end of the first surgical line to the first end of the connector;

coiling any excess length of the first surgical line within the housing; and connecting the second end of the connector to a second line at an external recess in the housing.

26. A device for supporting a separately-placed surgical line, the device comprising:

a base having an opening therein for receiving a separately-placed first surgical line extending from a subject;

a housing extending from the base, the housing having a substantially dome shape to form an enclosure for the base and for the opening in the base; and a connector fixed within a wall of the housing and having a first end connected to an end of the first surgical line and a second end connected to a second line, whereby the connector forms a conduit extending between the first and second ends through which fluids flow between the first surgical line and the second line, wherein the housing defines a space, the first end of the connector is located in the space, the end of the first surgical line is located in the space, and the second end of the connector is located outside of the housing; and wherein the housing has a removable lid to provide access to the space, the lid removable from the housing while the housing remains connected to the base.

27. The device according to claim 1, wherein the housing has a substantially dome shape to define a space with the first end of the connector located in the space, the end of the first surgical line located in the space, and the second end of the connector located outside of the housing.

* * * * *